US00PP26091P2

(12) United States Plant Patent
Lannes

(10) Patent No.: US PP26,091 P2
(45) Date of Patent: Nov. 17, 2015

(54) ***HIBISCUS* PLANT NAMED 'LANSEINE'**

(50) Latin Name: *Hibiscus rosa-sinensis*
Varietal Denomination: Lanseine

(71) Applicant: Robert Lannes, Malause (FR)

(72) Inventor: Robert Lannes, Malause (FR)

( * ) Notice: Subject to any disclaimer, the term of this patent is extended or adjusted under 35 U.S.C. 154(b) by 186 days.

(21) Appl. No.: 13/987,546

(22) Filed: Aug. 6, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

(56) References Cited

PUBLICATIONS

CPVO Community Plant Variety Office, Official Gazette of the Community Plant Variety Office Apr. 2011, pp. 32 and 49.*

* cited by examiner

*Primary Examiner* — June Hwu
(74) *Attorney, Agent, or Firm* — Penny J. Aguirre

(57) ABSTRACT

A new cultivar of *Hibiscus* named 'Lanseine', characterized by its large flowers that are deep red in color with a small darker red eye, its round shaped flowers that open fully, its short leaf internode lengths, its very dark green foliage, its good self-branching, and its vigorous growth habit.

2 Drawing Sheets

Botanical classification: *Hibiscus rosa-sinensis*.
Cultivar designation: 'Lanseine'.

BACKGROUND OF THE INVENTION

The present invention relates to a new and distinct cultivar of *Hibiscus* plant of hybrid origin, botanically known as *Hibiscus rosa-sinensis* 'Lanseine' and will be referred to hereafter by its cultivar name, 'Lanseine'. 'Lanseine' is a new cultivar of tropical *Hibiscus* grown for use as a landscape and container plant.

The new cultivar was developed through an on-going breeding program conducted by the Inventor in Malause, France. The objectives of the breeding program are to develop new cultivars of *Hibiscus* that exhibit compact plant habits with self-branching and a well-balanced plant habit.

The Inventor made a cross in July of 2006 between 'Vatican Rouge' (not patented) as the female parent and 'Casino Rouge' (not patented) as the male parent. 'Lanseine' was selected as a single unique plant from the resulting seedlings in September of 2009.

Asexual propagation of the new cultivar was first accomplished by stem cuttings in Malause, France in September of 2009 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics 'Lanseine'. These attributes in combination distinguish 'Lanseine' as a new and distinct cultivar of *Hibiscus*.

1. 'Lanseine' exhibits large flowers that are deep red in color with a small darker red eye.
2. 'Lanseine' exhibits round shaped flowers that open fully.
3. 'Lanseine' exhibits short leaf internode lengths.
4. 'Lanseine' exhibits very dark green foliage.
5. 'Lanseine' exhibits good self-branching.
6. 'Lanseine' exhibits a vigorous growth habit.

The female parent of 'Lanseine', 'Vatican Rouge', differs from 'Lanseine' in having smaller flowers that don't open completely and in having less self-branching. The male parent of 'Lanseine', 'Casino Rouge', differs from 'Lanseine' in having smaller flowers, less self-branching, and a less vigorous growth habit. 'Lanseine' can also be most closely compared to the cultivars 'Volcano' (not patented) and 'Barcelona' (not patented). Both are similar to 'Lanseine' in flower color. 'Volcano' differs from 'Lanseine' in having flowers that are smaller, more orange in color with a pink eye, and in having longer leaf internodes. 'Barcelona' differs from 'Lanseine' in having flowers that are smaller and lighter red in color (especially near petal edges), in having a less vigorous growth habit, and in blooming later in the season.

BRIEF DESCRIPTION OF THE DRAWINGS

The accompanying colored photograph illustrates the overall appearance and distinct characteristics of the new *Hibiscus*. The photographs were taken of a six month-old plant of 'Lanseine' as grown in a one-gallon container in a greenhouse in Malause, France.

The photograph in FIG. 1 provides a side view of 'Lanseine' in bloom.

Figure 1:
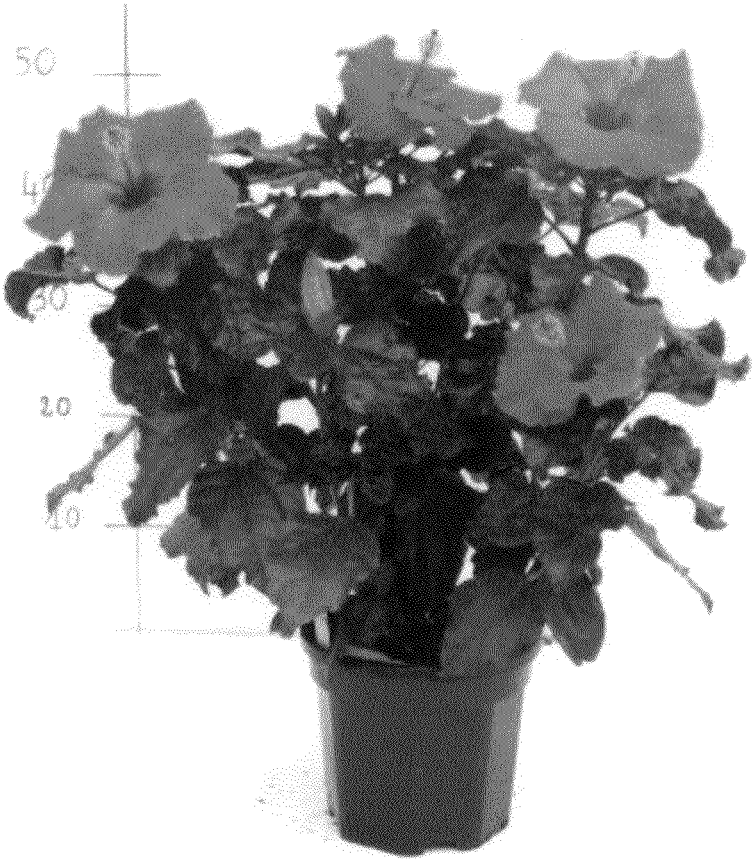
Figure 2:
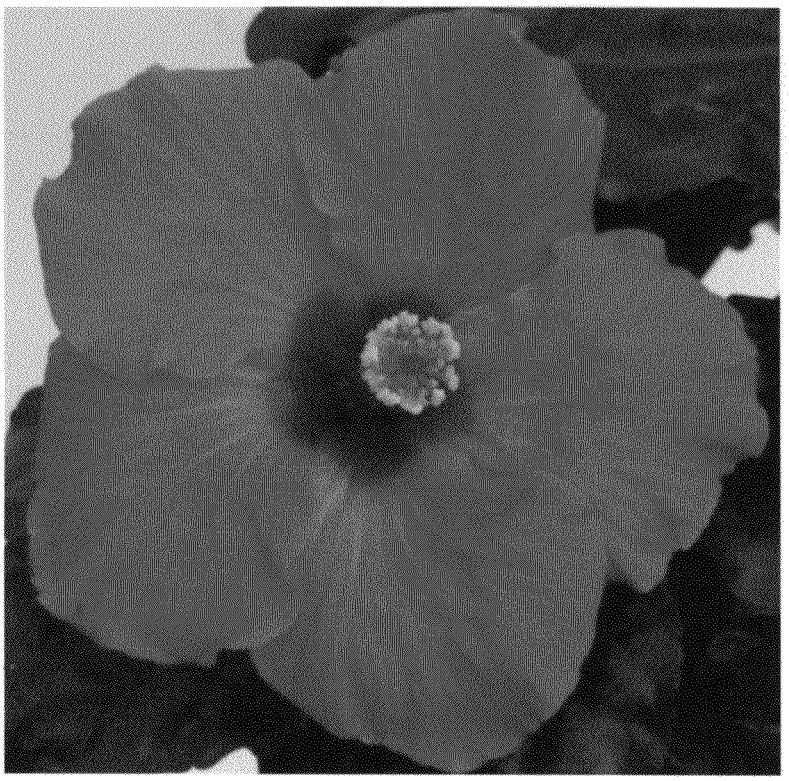

The photograph in FIG. 2 provides a close-up view of a flower of 'Lanseine'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 6 month-old plants of the new cultivar as grown in two-quart containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Continuously through summer in Grand Saline, Tex. and Malause, France.

*Plant type*.—Tropical evergreen shrub.

*Plant habit*.—Upright and slightly spreading, compact.

*Height and spread*.—Reaches 40 to 50 cm in height and 30 to 35 cm in spread.

*Hardiness*.—At least in U.S.D.A. Zones 9 to 11.

*Diseases*.—Not susceptible or resistance to diseases has been observed.

*Root description*.—Fibrous roots.

*Propagation*.—Stem cutting.

*Growth rate*.—Vigorous.

Stem description:

*Shape*.—Slightly oval.

*Stem color*.—New growth; 138B with overlay of 196B in some areas, mature wood; 156A with striations of 138C.

*Stem size*.—Main stems; an average of 12 cm in length and 8 mm in width, lateral stems; an average of 15 cm in length and 3.5 mm in diameter.

*Stem surface*.—New growth; very sparse hairs, bark; finely striated.

*Stem aspect*.—Held upright to an average angle of 15° (0°=vertical).

*Stem strength*.—Strong.

*Branching*.—Self-branching, an average of 2 main stems and 4 lateral branches per main stem in a two-quart container.

*Internode*.—Average of 2.2 cm.

Foliage description:

*Leaf shape*.—Ovate.

*Leaf division*.—Simple.

*Leaf base*.—Rounded.

*Leaf apex*.—Acute.

*Leaf venation*.—Pinnate, 138A to 138B in color on upper and lower surface.

*Leaf margins*.—Crenate and wavy.

*Leaf attachment*.—Petiolate.

*Leaf arrangement*.—Alternate.

*Leaf orientation*.—Held horizontal to slightly downward.

*Leaf aspect*.—Slightly cupped inward to flat.

*Leaf surface*.—Upper surface glabrous and glossy, lower surface sparsely pubescent and satiny.

*Leaf color*.—Young and mature leaves upper surface; a color between N137A and 139A, young and mature leaves lower surface; 137B.

*Leaf size*.—Average of 7.5 cm in length, and 5.2 cm in width.

*Leaf quantity*.—Up to 8 leaves per lateral branch 15 cm in length.

*Petioles*.—Average of 1.7 cm in length and 1.2 mm in diameter, 137A in color, finely pubescent surface.

Flower description:

*Inflorescence type*.—Flowers are solitary.

*Lastingness of flowers*.—About 1 day, self cleaning.

*Flower size*.—An average of 9 cm in depth (including reproductive organs, without 3.5 cm) and 12.5 cm in diameter.

*Flower fragrance*.—None.

*Flower shape*.—Rotate.

*Flower number*.—Average of 3 per lateral stem at one time, continuously produces throughout the summer.

*Flower aspect*.—Upright and horizontal when fully open.

*Flower bud*.—Elliptic in shape, an average of 5.5 cm in length and 3 cm in width, color sepal portion; a blend of 144A and 137C, apex (petal portion); a blend of 144B and suffused with 39B.

*Flower attachment*.—Peduncle.

*Petal number*.—5.

*Petal shape*.—Orbicular.

*Petal color*.—Upper surface when opening and fully opened; 34A with veins 63C near eye zone and eye zone 60A, lower surface when opening and fully opened; a blend of 34B and 28D and blending into 63C near base.

*Petal surface*.—Both surfaces smooth and dull on upper portion and satiny near base.

*Petal margins*.—Slightly wavy.

*Petal apex*.—Rounded.

*Petal base*.—Cuneate and slightly oblique and adnate to base of style.

*Petal size*.—Average of 7 cm in length and 6.7 cm in width.

*Sepal number*.—5.

*Sepal shape*.—Elliptic.

*Sepal margin*.—Entire.

*Sepal size*.—Average of 3 cm in length and 1 cm in width.

*Sepal aspect*.—Upright, lower 60% fused.

*Sepal surface*.—Outer surface puberulent, inner surface glabrous and glossy.

*Sepal apex*.—Cuspidate.

*Sepal base*.—Fused.

*Sepal color*.—Young and mature outer and inner surface; a blend of 144A and 137C.

*Calyx*.—Campanulate in shape, average of 3 cm in length and 3 cm in diameter.

*Peduncles*.—An average of 2 cm in length (including a 4 mm segment towards base of flower that is wider and separated by a ligule), about 2 mm in diameter, strong, average angle is upright to 45°, 137B in color with ligule 137A, very sparsely pubescent surface.

*Pedicels*.—Not present, flowers are solitary from terminal leaf axils.

*Bracts*.—Average of 5 bracts held upright surrounding sepals, oblong in shape, apiculate apex, truncate base, average of 1.4 cm in length and 3.5 mm in width, a color between N137B in color on inner and outer surface, surface is slightly pubescent on inner and outer surface.

Reproductive organs:

*Gynoecium*.—1 pistil, about 8 cm in length, stigmas; 5, club-shaped, and 60A in color with style arms 14D in color, 5 cm in length, and pubescent, style; 6 cm in length and 60A in color at base and 34A near apex, ovary; oblong in shape, 8 mm in length and 6 mm in width, a blend of 14D and 145D in color and completely covered by the base of the pistil style.

*Androecium*.—Stamens; average of 65, stamens are clustered and implanted into upper portion of style, anthers; dorsifixed and orbicular in shape, 1 mm in diameter, and 145D in color; filament; 4.5 mm in length, 0.3 mm in width, and 34B in color, pollen; abundant in quantity and 17C in color.

*Fruit/seeds*.—None observed.

It is claimed:

1. A new and distinct cultivar of *Hibiscus* plant named 'Lanseine' as herein illustrated and described.

* * * * *